(12) United States Patent
Wilfinger et al.

(10) Patent No.: US 8,989,874 B2
(45) Date of Patent: *Mar. 24, 2015

(54) BIOELECTRODE

(75) Inventors: Markus Wilfinger, Rum (AT); Burrhus Lang, Innsbruck (AT)

(73) Assignee: Leonh.Lang, Innsbruck (AT)

( * ) Notice: Subject to any disclaimer, the term of this patent is extended or adjusted under 35 U.S.C. 154(b) by 478 days.

This patent is subject to a terminal disclaimer.

(21) Appl. No.: 12/684,494

(22) Filed: Jan. 8, 2010

(65) Prior Publication Data

US 2010/0185078 A1 Jul. 22, 2010

(30) Foreign Application Priority Data

Jan. 20, 2009 (AT) .................................. 85/2009
Jul. 27, 2009 (AT) .................................. 1173/2009

(51) Int. Cl.
*A61N 1/05* (2006.01)
*A61B 5/0408* (2006.01)
*A61N 1/04* (2006.01)

(52) U.S. Cl.
CPC ....... *A61B 5/04087* (2013.01); *A61B 2562/125* (2013.01); *A61N 1/046* (2013.01); *A61N 1/048* (2013.01); *A61N 1/0492* (2013.01); *A61N 1/0496* (2013.01)
USPC ...................................................... 607/142

(58) Field of Classification Search
CPC ..... A61N 1/0472; A61N 1/048; A61N 1/042; A61N 1/044; A61N 1/0452; A61N 1/0456
USPC .......................................... 607/142, 149, 152
See application file for complete search history.

(56) References Cited

U.S. PATENT DOCUMENTS 3,547,105 A 12/1970 Paine
(Continued)

FOREIGN PATENT DOCUMENTS

DE 2612130 A1 10/1976
EP 0097436 A1 1/1984
(Continued)

OTHER PUBLICATIONS

Internet Citation, "Typical Properties for 3M Electrically Conductive Adhesive Films", Feb. 1, 2000, URL: http://multimedia.3m.com/mws/mediawebserver?66666UuZjcFSLXTtmXfVMxT2EVuQEcuZgVs6EVs6E666666 (found on Mar. 9, 2010).
European Search Report of Corresponding European Application, EP No. 10 00 0126, dated Apr. 29, 2010.
(Continued)

*Primary Examiner* — Paula J Stice
(74) *Attorney, Agent, or Firm* — Novak Druce Connolly Bove + Quigg LLP; Thomas M. Saunders

(57) ABSTRACT

A bioelectrode comprising:
a skin-side, electrically conducting adhesive layer and
a flexible electrical connecting cable which in an electrically insulating cable sheath includes at least one electrical conductor,
wherein fitted at the electrode-side end of the connecting cable is a preassembled electrical conducting element electrically connected to the electrical conductor of the connecting cable, wherein the preassembled electrical conducting element is electrically connected in the installed condition to the skin-side, electrically conducting adhesive layer.

19 Claims, 4 Drawing Sheets

(56) References Cited

U.S. PATENT DOCUMENTS

| | | |
|---|---|---|
| 4,008,721 A | 2/1977 | Burton |
| 4,092,985 A * | 6/1978 | Kaufman .................. 606/32 |
| 4,736,752 A * | 4/1988 | Munck et al. ............... 607/152 |
| 5,269,810 A | 12/1993 | Hull et al. |
| 5,857,858 A | 1/1999 | Gorowitz et al. |
| 6,336,049 B1 * | 1/2002 | Kinbara et al. ............. 607/148 |
| 7,742,828 B2 * | 6/2010 | Gadsby et al. .............. 607/142 |
| 2002/0006358 A1 | 1/2002 | Sugiyama |
| 2003/0199947 A1 * | 10/2003 | Gardner et al. ............. 607/96 |
| 2005/0015134 A1 * | 1/2005 | Carim ....................... 607/142 |
| 2006/0040427 A1 | 2/2006 | Ferrari |
| 2006/0095001 A1 * | 5/2006 | Matsumura et al. ........ 604/20 |

FOREIGN PATENT DOCUMENTS

| | | |
|---|---|---|
| EP | 0313173 A1 | 4/1989 |
| EP | 0337667 A1 | 10/1989 |
| EP | 1813306 A1 | 8/2007 |
| WO | WO 02/39894 | 5/2002 |

OTHER PUBLICATIONS

Austrian Patent Office Search Report of corresponding Austrian Patent Application No. A 85/2009 dated Aug. 21, 2009.

Austrian Patent Office Search Report of corresonding Austrian Patent Application No. A 85/2009 dated Jan. 25, 2010.

* cited by examiner

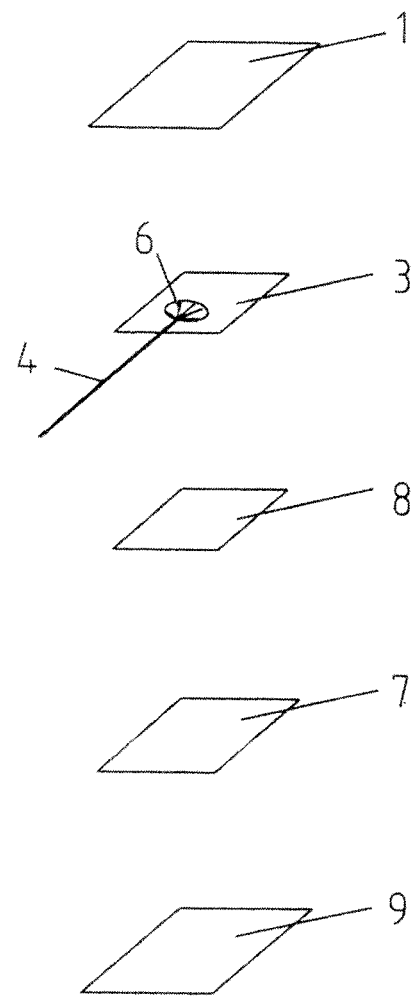
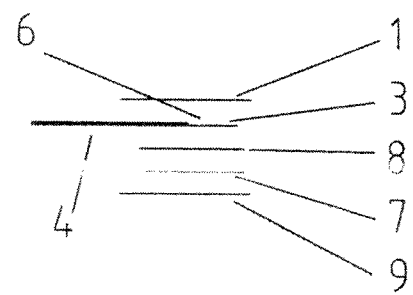

BIOELECTRODE

CROSS-REFERENCE TO RELATED APPLICATIONS

This application claims priority to A 85/2009 AT filed Jan. 20, 2009 and to A 1173/2009 AT filed Jul. 27, 2009.

FIELD OF THE INVENTION

The invention comprises a bioelectrode comprising a skin-side, electrically conducting adhesive layer and a flexible electrical connecting cable which in an electrically insulating cable sheath includes at least one electrical conductor, preferably in the form of a braid comprising a plurality of individual wires or conducting individual fibers. The invention further concerns a process for the production of such an electrode.

BACKGROUND

Bioelectrodes are used in many ways. Either current is fed to the human or animal body as in the case of a defibrillation electrode or stimulation electrode or current is carried off from the body (for example neutral electrodes or measurement electrodes).

The object of the invention is to provide a bioelectrode in which the electrical connecting cable has a good mechanical hold in the electrode and also good electrical contact is ensured in relation to those layers of the electrode, which finally feed the current to the skin or take it therefrom.

SUMMARY OF THE INVENTION

According to the invention that is achieved in that fitted at the electrode-side end of the connecting cable is a preassembled electrical conducting element electrically connected to the electrical conductor of the connecting cable, wherein the preassembled electrical conducting element is electrically connected in the installed condition—possibly with the interposition of at least one further electrically conducting layer— to the skin-side, electrically conducting adhesive layer.

The electrical conducting element according to the invention can be connected to the electrical connecting cable mechanically firmly and in good electrically conducting relationship, prior to assembly of the actual bioelectrode, in a separate working process. Preferably the electrical conducting element comprises a flat layer of electrically conductive, thermoplastic material. The end of the connecting cable can be enclosed for example by a hardenable material and can thus form the preassembled electrical conducting element. It is however also possible for a thermoplastic layer which is already present to be thermally welded to the end of the connecting cable or welded thereto by means of the action of ultrasound. At any event that involves an electrically conducting area of the electrical conducting element, that is enlarged in relation to the conductor of the connecting cable. That means that the preassembled electrical conducting element can be well anchored in the bioelectrode.

The preassembled electrical connecting element also makes it possible for the current which is supplied by way of the electrical connecting cable to be uniformly distributed over a larger area or taken off from a larger area. It is even possible for a specific resistance profile to be incorporated in the electrically conducting layer of the connecting element, which layer can also comprise a plurality of sublayers, for example in such a way that the surface resistance decreases or increases as required from the central connecting point of the electrode-side cable end towards the edge. At any event a specifically targeted current distribution in relation to area is possible.

Further advantages and details of the invention are set forth more fully with reference to the specific description hereinafter.

BRIEF DESCRIPTION OF THE DRAWINGS

FIG. 4a shows a fourth embodiment by way of example of the invention as a diagrammatic exploded view and FIG. 4b shows the electrode of FIG. 4a as a diagrammatic cross-sectional view.

DETAILED DESCRIPTION OF THE INVENTION

Figure 1A:
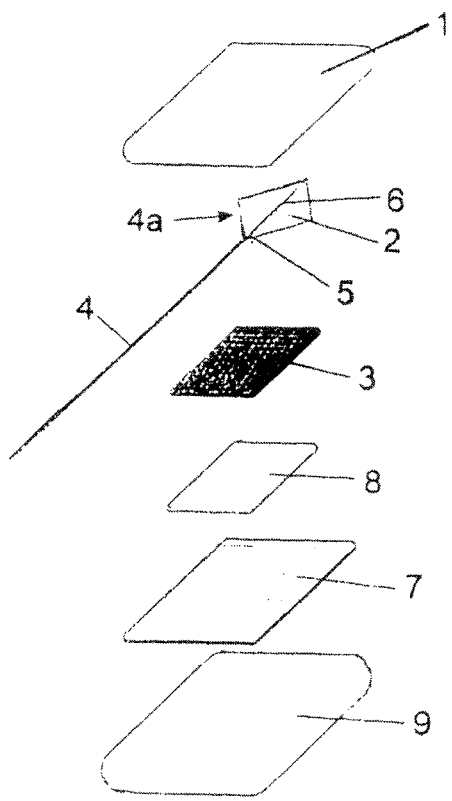
FIG. 1a shows a first embodiment by way of example of the invention as a diagrammatic exploded view.
Figure 1B:
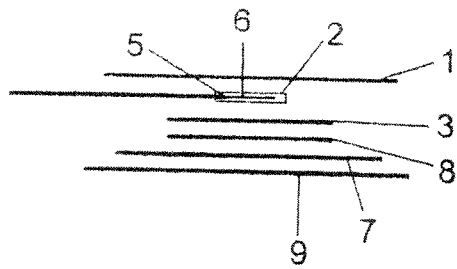
FIG. 1b shows the FIG. 1a electrode as a diagrammatic cross-sectional view.

FIGS. 1a and 1b show a first embodiment by way of example of an electrode according to the invention, in particular a defibrillation electrode.

The electrode in FIGS. 1a and 1b has beneath a carrier material 1 (for example foam material comprising polyethylene or similar, a film comprising polyethylene terephthalate or the like) a thermoplastic layer 3, which is electrically conducting. The thermoplastic layer 3 can comprise for example: polyvinyl chloride, acrylonitrile butadiene styrene, polyurethane, polyethylene or the like. The electrical conductivity of the thermoplastic layer 3 can be achieved for example by metallic inclusions or inclusions on a carbon basis (carbon black, graphite). The electrical resistance across the electrode can be varied by suitable distribution of such inclusions or a multi-layer configuration in respect of the layer 3.

In accordance with the invention an electrical conducting element is preassembled at the electrode-side free end 4a of the connecting cable 4. In the embodiment shown in FIGS. 1a and 1b the electrical conducting element 2 comprises a hardened (preferably thermoplastic) electrically conducting material which is connected to the cable end 4a mechanically firmly and in good electrically conducting contact. The electrically conducting material in which the cable end is arranged, preferably being cast therein, is preferably of a layer-shaped configuration. That flat configuration allows good installation in the bioelectrode, in which case, with a good mechanical holding action, it is also possible to produce good electrical contact (in FIG. 1a, with respect to the electrically conducting layer 3). In that arrangement the electrical conducting element 2 is of small structural height. In this case small structural height means that the electrical conducting element 2, jointly with the cable end 4a, is of a layer thickness of between 50 and 250 micrometers, preferably between 50 and 200 micrometers. That joint layer thickness of the cable end 4a and the conducting element 2 applies in the entire bioelectrode, that is to say in the region between the skin-side adhesive layer 7 and a non-conducting carrier material 1. If the layer thickness were to be below 50 micrometers, that would lead to problems in the welding operation. With an excessively thick conducting element (over 250 micrometers) flexibility of the electrode is no longer guaranteed, that is to say adaptability to the human body is lost or is reduced.

It is pointed out that the cross-sectional view in FIG. 1b only shows the layer sequence, but the individual layers of the electrode can naturally bear directly against each other and be connected to each other.

Figure 1C:
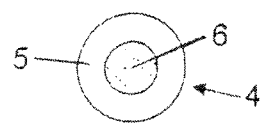
FIG. 1c shows a cable cross-section.

As shown in cross-section in FIG. 1c the electrical connecting cable 4 includes an electrically insulating cable sheath 5 in which there is at least one electrical conductor 6. Preferably that electrical conductor 6 is a braid comprising a plurality of individual wires/individual fibers.

Materials which can be used for the insulating cable sheath are polyethylene, polypropylene or polyvinyl chloride or the like. The conducting wires can be carbon fiber strands which comprise several 1000 to several 10,000 individual fibers which can be metallised. Metal braids alone or metal braids combined with carbon fibers can also be used as conducting wires.

Such a cable configuration makes it possible for the cable end to be stripped of insulation for example over a length of between 0.5 cm and 5 cm so that the conductor 6 is exposed. The preassembled electrical conducting element 2 is then preferably connected not only to the stripped conductor region but also to a part of the insulating cable sheath 5. It is possible in that way to still further enhance the mechanical hold between the cable end 4a and the electrical conducting element. For the same purpose it would also be conceivable to fan open the individual wires of the braid of the conductor and thus achieve an improved holding action and improved electrical contact in the casting material layer of the electrical conducting element 2.

Moreover it should be mentioned that the electrical conductivity of the preferably thermoplastic layer of the electrical conducting element 2 can be achieved, as is already the case with the layer 3, by metallic inclusions and/or inclusions on a carbon base (carbon black, graphite). It is also possible to vary the electrical resistance over a certain surface region by suitable distribution of such inclusions or by virtue of a multilayer nature for the electrical conducting element 2.

The layer thickness of the electrical conducting element is preferably of the order of magnitude of between 100 and 250 micrometers. That layer thickness applies both to the electrical conducting element 2 on its own and also the electrical conducting element 2 together with the cable 4 or electrical conductor 6 arranged therein or thereon. As shown in FIGS. 1b, 2b and 3b the cable end 4b or the electrical conductor 6 is enclosed by the electrical conducting element 2. However, there is no intention to exclude that electrical conductor 6 or the cable end 4a bearing against the electrical conducting element 2 on or under same, in which case the total layer thickness does not however exceed 250 micrometers. That affords the advantage of much greater flexibility and a much smaller maximum thickness for the bioelectrode, in particular, in relation to EP 0 337 667 B1 known from the state of the art.

At the skin side the bioelectrode shown in FIGS. 1a through 1b has a conductive adhesive layer 7, preferably in the form of a conductive gel. The conductive adhesive layer which must be biocompatible can be both an adhesive hydrogel and also a conductive adhesive.

A metal layer or a metal/metal chloride layer can be arranged between the skin-side conductive adhesive layer 7 and the electrically conducting thermoplastic layer 3, the metal preferably being silver. That layer is denoted by reference 8.

Arranged beneath the conductive adhesive layer 7 is a cover material 9 which can be pulled off and which protects the conductive adhesive layer upon transport and in storage and which is pulled off prior to use. That cover material can comprise plastic materials such as polyethylene terephthalate, polystyrene, polypropylene or the like, which can also be siliconised.

Figure 2A:
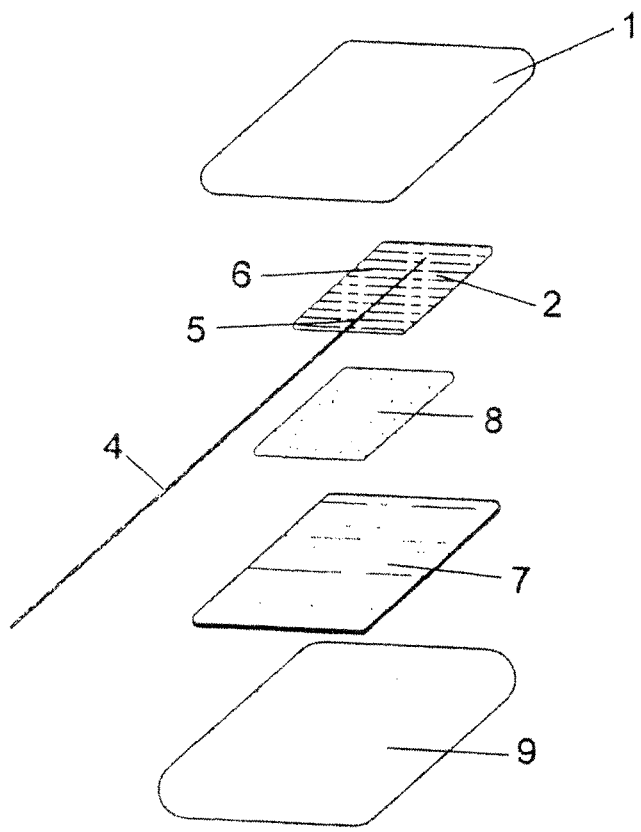
FIG. 2a shows a second embodiment by way of example of the invention as a diagrammatic exploded view and FIG. 2b shows the electrode of FIG. 2a as a diagrammatic cross-sectional view.
Figure 2B:
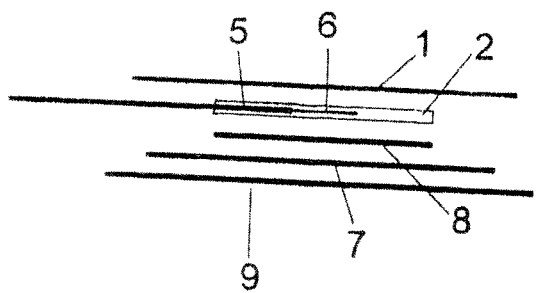

The second embodiment shown in FIGS. 2a and 2b differs from the first embodiment of FIGS. 1a and 1b substantially by a different configuration of the preassembled electrical conducting element 2 and by virtue of the fact that the electrical conducting thermoplastic intermediate layer 3 is omitted so that the preassembled electrical conducting element bears directly on the layer 8. In this embodiment as shown in FIGS. 2a and 2b the preassembled electrical conducting element is of a comparatively large area which is already more than 50%, preferably more than 70%, of the area of the skin-side, electrically conducting adhesive layer 7.

In addition, in the embodiment shown in FIGS. 2a and 2b, the electrical conducting element 2 has been produced in a step preceding the electrode construction operation, in that the electrical conductor of the connecting cable 4 has been welded to a thermoplastic, electrically conductive layer. For example thermal welding processes or ultrasound welding processes are suitable for the welding operation. At any event this ensures that the cable end involves a good mechanical connection to the electrically conductive layer of the preassembled electrical conducting element 2.

The electrical conducting elements according to the invention can be produced in an optimised fashion in terms of the process in large numbers in a separate working procedure. In the subsequent actual production of the electrode, namely assembly of the layers as shown in FIGS. 1a, 2a and 3a respectively by welding or adhesive, those preassembled electrical conducting elements together with the cable end can then be easily inserted, which allows rapid production at a high cycle rate.

Figure 3A:
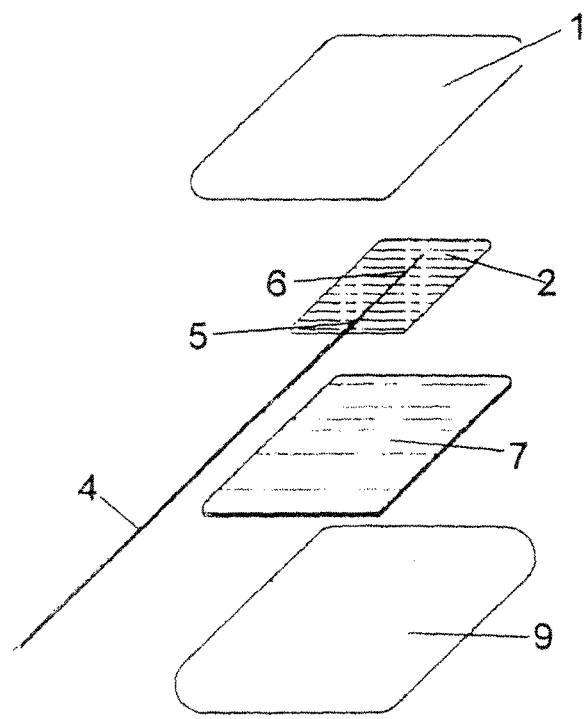
FIG. 3a shows a third embodiment by way of example of the invention as a diagrammatic exploded view and FIG. 3b shows the electrode of FIG. 3a as a diagrammatic cross-sectional view.
Figure 3B:
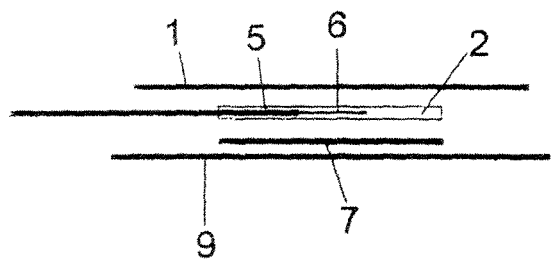

In the third embodiment of FIGS. 3a and 3b, the layer 8 is omitted, in comparison with the second embodiment of FIGS. 2a and 2b. Accordingly the preassembled electrical conducting element 2 bears directly on the top side of the skin-side, electrically conducting adhesive layer 7. The embodiment of FIGS. 3a and 3b is distinguished by a low number of layers. The structure is particularly simple and thus inexpensive. Nonetheless a good mechanical hold for the cable end in the electrode is ensured by the preassembled electrical conducting element 2. In addition, good current distribution can be achieved over the skin-side, electrically conducting adhesive layer 7 by virtue of the preassembled electrical conducting element 2 being of a corresponding flat configuration.

In the fourth embodiment of FIGS. 4a and 4b the preassembled electrical conducting element is formed by the layer 3. There are two different production processes in relation to this embodiment.

In a first variant the fanned-open individual wires of the braid of the conductor are connected to the preassembled electrical conducting element 3 by means of an electrically conductive lacquer layer, preferably a layer of carbon lacquer. The lacquer dries and thereby holds the individual wires of the braid intimately to the preassembled electrical conducting element 2. That lacquer can comprise polyurethane or polyvinyl chloride binding agent or can include such constituents. To permit conductivity of the lacquer itself fillers such as for example carbon fibers, carbon black, graphite, metal pigments and so forth can be included therein.

As an alternative thereto, if the electrical conducting element 3 is in the form of a binding agent-bearing film (for example of carbon film), the electrical conducting element 3 can be solubilised by a suitable solvent in that region where the individual wires of the braid are to be secured, whereby the binding agent of the film takes over the task of the above-described lacquer. Esters or ketones can be used as the solvent.

In both cases no further electrically conducting layer 8 is required. Nonetheless it may be advantageous (for current distribution and handling) to use a further electrically conducting and preferably thermoplastically weldable layer 8.

In a further variant the process according to the invention is distinguished in that firstly a preferably layer-form electrical conducting element 2 is fitted at the electrode-side cable end 4a. It is only thereafter that that preassembled electrical conducting element is connected to at least one further layer of the bioelectrode, preferably by welding or adhesive.

As is actually apparent from all views the electrical conducting element 2 is arranged substantially centrally in the bioelectrode, that is to say the electrical conducting element 2 is spaced at all sides from the edge of the bioelectrode or the outermost layers 1 and 7 or 1 and 9 respectively. That spacing should remain the same as far as possible all around. Preferably that spacing is between 3 and 20 mm, preferably between 5 and 15 mm. That arrangement of the electrical conducting element 2 as far as possible in the center of the overall bioelectrode affords very good current distribution over the entire bioelectrode region or in particular on the electrically conducting adhesive layer 7.

It will be appreciated that the invention is not limited to the illustrated embodiments. For example the invention is suitable not only for defibrillation electrodes and electrodes which feed current to the skin (for example: stimulation electrodes) but basically also for electrodes which take current from the skin (for example neutral electrodes, measurement electrodes). The layer structure and the size relationships can differ from the illustrated embodiments. What is essential is that there is preassembled at the electrode-side end of the connecting cable an electrical conducting element which ensures a good mechanical hold and a good electrical connection in the electrode.

The invention claimed is
1. A bioelectrode comprising:
a flexible electrical connecting cable in an electrically insulating cable sheath, the flexible electrical connecting cable comprising an electrical conductor braid whose individual wires are fanned open;
an electrical conduction element fitted at an electrode-side end of the flexible electrical connecting cable, wherein the electrical conduction element is in direct contact with and electrically connected to the flexible electrical connecting cable; and
an electrically conductive adhesive layer configured to be attached to a skin of a patient, wherein the electrical conduction element, in an installed condition, is attached and electrically connected to the electrically conductive adhesive layer.

2. The bioelectrode of claim 1, wherein the electrical conduction element is formed from an electrically conductive layer.

3. The bioelectrode of claim 2, wherein the electrically conductive layer comprises an electrically conductive thermoplastic material.

4. The bioelectrode of claim 1, wherein the electrical conduction element is connected to the flexible electrical connecting cable by way of an electrically conductive lacquer layer.

5. The bioelectrode of claim 4, wherein one of the electrical conduction element and the electrical conductor is provided with an electrically conductive lacquer layer, and the electrical conductor is placed on the electrical conduction element so that the electrical conductor is connected to the electrical conduction element by drying of the lacquer layer.

6. The bioelectrode of claim 1, wherein the electrical conduction element is in a form of a film comprising a binding agent, and wherein the flexible electrical connecting cable is connected to the electrical conduction element by the binding agent.

7. The bioelectrode of claim 6, wherein the electrical conducting element comprises a film bearing a binding agent and solubilised by a solvent, and wherein the electrical conductor is placed on a solubilized region of the film so that the electrical conductor is connected to the electrical conduction element by drying of the binding agent.

8. The bioelectrode of claim 1,
wherein the flexible electrical connecting cable is welded to a thermoplastic electrically conductive layer, and wherein the thermoplastic electrically conductive layer forms part of the electrical conduction element.

9. The bioelectrode of claim 1, wherein the flexible electrical connecting cable comprises an electrical conductor within an electrically insulating cable sheath, and wherein the electrode-side end is stripped so that the electrical conductor is exposed over a length between 0.5 cm and 5 cm to form a stripped conductor region, and wherein the electrical conduction element is connected to the stripped conductor region and also to the electrically insulating cable sheath.

10. The bioelectrode of claim 1, wherein the electrical conduction element is welded to an electrically conductive thermoplastic intermediate layer which is electrically connected to the electrically conductive adhesive layer.

11. The bioelectrode of claim 10, wherein a thermoplastic material of one of the electrical conduction element and the electrically conductive thermoplastic intermediate layer is electrically conductive by one of a metal inclusion and a carbon-based inclusion.

12. The bioelectrode of claim 1, wherein the electrically conductive adhesive layer comprises one of a conductive hydrogel and electrically conductive adhesive.

13. The bioelectrode of claim 1, wherein one of a metal layer and a metal/metal chloride layer is arranged above a top side of the electrically conductive adhesive layer which is opposite of the skin.

14. The bioelectrode of claim 13, wherein the one of the metal layer and the metal/metal chloride layer comprises silver.

15. The bioelectrode of claim 1, wherein a cover material which can be pulled off is arranged beneath the electrically conductive adhesive layer.

16. The bioelectrode of claim 1, wherein an electrically non-conducting carrier material is arranged on top of the electrode-side end, wherein the electrically non-conducting carrier material is remote from the skin.

17. The bioelectrode of claim 1, wherein the bioelectrode is a defibrillation electrode, and wherein an area of a layer that is arranged on a side, remote from the skin, of the electrically conductive adhesive layer is preferably at least 50 cm$^2$ in size.

18. The bioelectrode of claim 1, wherein the flexible electrical connecting cable comprises an electrical conductor, wherein the electrical conduction element and the electrical conductor form a joint layer configuration, wherein the electrical conductor is arranged one of in the electrical conduction element and on the electrical conduction element, and wherein the joint layer configuration is of thickness of between 50 and 250 micrometers.

19. The bioelectrode of claim 18, wherein a thickness of the joint layer configuration in a total region between the electrically conductive adhesive layer and a non-conducting carrier material of the bioelectrode does not exceed 250 micrometers.

* * * * *